United States Patent [19]

Schmidt

[11] 4,424,369
[45] Jan. 3, 1984

[54] SUBSTITUTED PYRAN-2-ONES

[75] Inventor: Hans-Georg Schmidt, Niederkassel, Fed. Rep. of Germany

[73] Assignee: Dynamit Nobel AG, Troisdorf, Fed. Rep. of Germany

[21] Appl. No.: 282,689

[22] Filed: Jul. 13, 1981

Related U.S. Application Data

[62] Division of Ser. No. 218,593, Dec. 19, 1980, Pat. No. 4,348,535.

[30] Foreign Application Priority Data

Dec. 22, 1979 [DE] Fed. Rep. of Germany ....... 2952068
Dec. 3, 1980 [DE] Fed. Rep. of Germany ....... 3045455
Dec. 6, 1980 [DE] Fed. Rep. of Germany ....... 3046059

[51] Int. Cl.³ .......................................... C07D 309/30
[52] U.S. Cl. ..................... 549/273; 549/294
[58] Field of Search ............................. 549/273, 294

[56] References Cited

U.S. PATENT DOCUMENTS 3,056,802 10/1962 Phillips et al. ................... 260/343.5
4,041,049 8/1977 Müller et al. .................................. λ
4,235,780 11/1980 Kondo et al. ........................ 560/177

Primary Examiner—Jane T. Fan
Attorney, Agent, or Firm—Sprung, Horn, Kramer & Woods

[57] ABSTRACT

There are disclosed substituted lactones of the formula

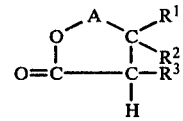

wherein A stands for —CH—CH$_2$X (X being Cl, Br or OH), —CHY—CHY—(Y being Cl or Br), or

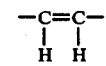

and R$^1$, R$^2$ and R$^3$ are the same or different radicals from the group of hydrogen and C$_1$ to C$_{10}$ alkyls, at least one of the radicals R$^1$, R$^2$ and R$^3$ being such an alkyl radical, and process for making the same.

5 Claims, No Drawings

SUBSTITUTED PYRAN-2-ONES

This is a division, of application Ser. No. 218,593, filed Dec. 19, 1980, now U.S. Pat. No. 4,348,535 issued Sept. 7, 1982.

This invention relates to substituted lactones of the formula

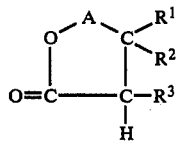

wherein A stands for

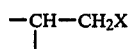

wherein X is chlorine, bromine or hydroxy, or —CHY—CHY— wherein Y represents chlorine or bromine, or

wherein $R^1$, $R^2$ and $R^3$ each independently represent hydrogen or a $C_1$ to $C_{10}$ alkyl group, with the proviso that in the cases of =$>$CH—$CH_2$A, and —CH=CH— at least one of said radicals $R^1$, $R^2$ and $R^3$ being such an alkyl radical.

This invention further relates to a process for the preparation of such substituted lactones wherein all radicals $R^1$, $R^2$ and $R^3$ represent hydrogen or none or only one or two of the radicals $R^1$, $R^2$ and $R^3$ are hydrogen and the remaining radicals $R^1$, $R^2$ or $R^3$ are straight chained or branched alkyl radicals with 1 to 10 carbon atoms and A represents the moiety —CH=CH—. or

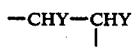

The invention further relates to the preparation of a substituted lactone of the formula (I) given above wherein A represents

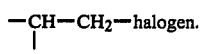

—CH—$CH_2$OH. In these processes novel compounds of the formula

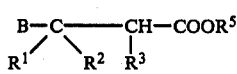

are provided wherein B stands for

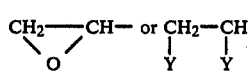

or $C_1$-$C_4$ alkyl and $R^1$, $R^2$ and $R^3$ are hydrogen or $C_1$-$C_{10}$ alkyl, wherein at least one of $R^1$, $R^2$ and $R^3$ is alkyl and $R^5$ is $C_1$-$C_4$ alkyl or an alkali metal or alkaline earth metal or hydrogen. These compounds can be considered as pentane carboxylic acid derivatives. Furthermore, this invention relates to such pentane carboxylic acids of the formula given above wherein B stands for

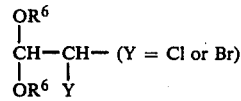

wherein $R^6$ is an alkyl radical of 1 to 10 carbon atoms.

The acetals of the formula given above wherein the radical B stands for

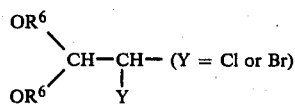

are obtained by reacting a substituted lactone of formula (I) wherein A stands for

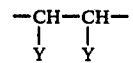

with an alkali or alkaline earth metal alcoholate in the presence of a super-stoichiometric amount of an aliphatic alcohol, e.g. alkanol with 1 to 10 carbon atoms. The preferred alcoholate for the reaction is an alkali metal alcoholate, especially sodium alcoholate. The amount of alcohol may be varied between a 2- to 200-fold molar excess. The reaction temperature is generally between +10° and +60° C. The acetals obtained by this reaction are isolated by fractional distillation. If no excess alcoholate is present, this distillation can be carried out directly subsequent to the reaction. In the presence of excess alcoholates it is, however, preferable to remove these by extraction with water and to subsequently separate the raw product by distillation.

In the preparation of the compounds of the substituted lactones of formula (I) wherein A stands for

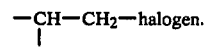

pentene carboxylic acid esters of the general formula

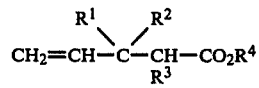

wherein $R^1$, $R^2$ and $R^3$ stand for the named alkyl radicals or wherein $R^1$, $R^2$ and $R^3$ represent hydrogen, and $R^4$ stands for an alkyl radical having from 1 to 4 carbon atoms, are initially reacted with halogen to give a compound of the general formula

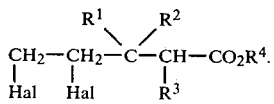

$$CH_2-CH_2-C-CH-CO_2R^4.$$
$$\ \ |\ \ \ \ \ \ \ |\ \ \ \ \ \ |$$
$$Hal\ \ Hal\ \ R^3$$

Hal meaning Cl or Br and $R^1$, $R^2$, $R^3$ and $R^4$ have the meaning given above. The addition product so obtained is then heated, which results in the formation of lactones of the general formula

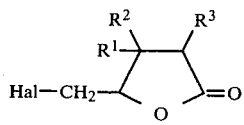

(II)

The addition of halogen to the pentene carboxylic acid ester is carried out, in a manner which as such is known, in an organic solvent, and preferably in a liquid chlorinated hydrocarbon such as $CCl_4$, by metering in the halogen at temperatures ranging from $-10°$ to $+40°$ C. At the end of the reaction, the solvent is eliminated by distillation. Generally speaking, the pressure in the reaction can be from 160 Torr to 3 atmospheres absolute with atmospheric pressure preferred. A stoichiometric amount of the halogen, especially chlorine and bromine, is used. Preferably the halogen is employed in an amount of up to one mole per mole of pentene carboxylic acid.

Ring formation to form the lactones of formula (II) takes place at temperatures ranging from 150° to 200° C. A solvent such as Decalin can be used but may also be dispensed with. Heating results in a low-boiling product which is preferably eliminated promptly from the reaction mixture by distillation. The halogen addition product is advantageously heated without isolation but can also be isolated. Heating is effected generally for at least 30 minutes, preferably 180 to 600 minutes.

For the preparation of lactones of formula (I) wherein A stands for

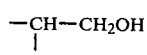

and $R^1$, $R^2$ and $R^3$ may be any radical from the group $C_1$ to $C_{10}$ alkyl or hydrogen, lactones of the formula (I) wherein A is

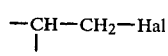

are first reacted with basic media to give compounds of the general formula

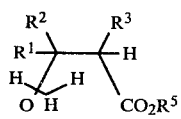

(III)

wherein $R^1$, $R^2$ and $R^3$ may be any radical of the group $C_1$ to $C_{10}$ alkyl or hydrogen and $R^5$ stands for an alkyl radical having from 1 to 4 carbon atoms, hydrogen, or an alkali metal or alkaline earth metal. A treatment with acid then results in lactone formation.

The treatment with basic media which results in ring contraction, that is to say, in the formation of the epoxide, is carried out at temperatures ranging from $-10°$ to $+50°$ C. The basic media used are alkali metal or alkaline earth metal alcoholates, carbonates or hydroxides. Preferred alcoholates are alkali metal or alkaline earth metal alcoholates of alcohols of 1 to 10 carbon atoms, especially alkali metal alkanolates, e.g. sodium methylate. Solvents such as alcohols, ethers or water are preferably used. The bases are used stoichiometrically or in excess.

If the reaction is carried out with an alcoholate as basic medium, pentane carboxylic acid ester is obtained. If in this reaction alcohol is used as solvent, an alcohol is preferably selected which corresponds to the alcohol component of the alcoholate. This has preferably 1 to 4 carbon atoms.

The lactones of formula (I) wherein A is

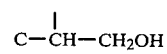

are prepared from the thus directly-obtained epoxides by stirring the epoxide of formula (III) into an acidic medium, such as dilute mineral acids or dilute organic acids. The acids are preferably used in a solvent. Apart from the preferably used water, the solvent may be an organic solvent such as an alcohol, ether, glacial acetic acid, carbon tetrachloride and the like.

The acids are effective even in catalytic amounts but may, if desired, be used in considerable excess. The preferred amounts range from 0.01 to 10 mole percent. The reaction temperature may range from as low as $-10°$ C. to as high as $+200°$ C. Suitable for use as acids are both Lewis and Broenstad acids such as $AlCl_3$, $BF_3$, $H_2SO_4$, $H_3PO_4$, $HNO_3$ and organic carboxylic acids.

The epoxide formed is best treated with acid immediately without isolation. It can, however, be formed by isolating the epoxide and treating the isolated epoxide with acid.

The preparation of the lactones of formula (I) wherein A is $-CH=CH-$ is effected through thermolysis of lactones of formula (I) wherein A is

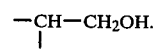

It is preferably carried out in the temperature range from 200° to 500° C.

The starting compound is preferably trickled through a heated tube filled with a heat-resistant material, for example, a ceramic material. The thermolysis is preferably carried out in an inert gas atmosphere. Pressures of 20 Torr to 4 atmospheres absolute are useful, especially atmospheric pressure.

The starting compounds may be used as is or as solutions. Preferred solvents are thermostable compounds such as liquid aromatic hydrocarbons, for example, benzene, toluene or xylene. During the reaction, water is split off, which may be eliminated prior to distillative working up when solvents which are immiscible with water are used.

Compounds of the general formula (I), wherein the radical A stands for

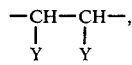

are prepared from compounds of formula (I) by adding halogens to the corresponding non-halogenated lactone with the double bond. This addition is preferably carried out in a liquid chlorinated hydrocarbon, as, for example, a carbon tetrachloride. The reaction temperature should if possible not exceed +40° C. Generally the temperature ranges from −50° to +40° C., especially −10° to +40° C. On completion of the addition the solvent is removed by distillation. The addition product is obtained in some cases in the residue as solid product, in such purity that it permits a direct subsequent treatment. If desirable it can be recrystallized. In other cases it must be distilled.

This dihalogenvalerolactone is in turn an intermdiary product for the above-mentioned acetates which correspond to the formula

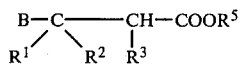

in which the radical B stands for

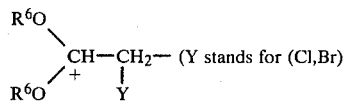

The alkyl-substituted pentene-4-carboxylic acid esters mentioned earlier are readily prepared by the reaction of appropriately substituted allyl alcohols with correspondingly substituted orthoacetic acid alkyl esters. (Tetrahedron Letters [1977], page 2543).

The novel lactones of general formula (I) are useful intermediates in the manufacture of plant protectants, pharmaceuticals and dyes.

This invention further relates to compounds of the formula

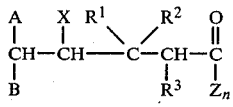 (III)

wherein n=0 or 1, and when n=1, A=B=Z=OR wherein each R is independently an alkyl residue of 1 to 4 carbon atoms and X is chlorine or bromine and $R^1$, $R^2$, and $R^3$ are hydrogen and/or an alkyl group of 1 to 10 carbon atoms. Where n=0 A=X and X is chlorine or bromine and B is an oxygen atom wherein the free valence of oxygen atom is linked with the free valence from the carbon atom.

In particular, there is contemplated halogen substituted lactones of the formula

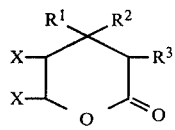 (IV)

wherein each $R^1$, $R^2$, and $R^3$ is independently hydrogen or an alkyl group of 1 to 10 carbon atoms and X is chlorine or bromine. In such instance, the compound of formula III supra is one wherein n=0. It corresponds to the compounds of formula I, wherein A stands for

Also contemplated are substituted carboxylic acids falling within formula III above wherein n=1. These substituted carboxylic acids have the formula

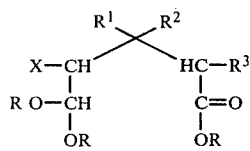 (V)

wherein each R moiety is independently an alkyl group of 1 to 4 carbon atoms and each $R^1$, $R^2$ snd $R^3$ is independently hydrogen and/or an alkyl group of 1 to 10 carbon atoms and X is chlorine or bromine. They correspond to the acetats mentioned above in this disclosure, wherein B stands for

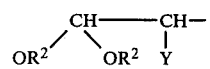

Halogen-substituted lactones of formula (V) above can be prepared from a compound of the formula

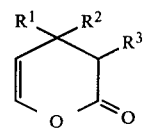 (VI)

wherein $R^1$, $R^2$ and $R^3$ are independently hydrogen and/or alkyl of 1 to 10 carbon atoms by contacting the same in an inert reaction mixture with chlorine or bromine. Preferably the reaction is conducted at a temperature between −10° and 40° C. Generally speaking, the chlorine or bromine is employed in a stoichiometric amount but can be employed in excess. An inert organic solvent is generally employed for this reaction. Particularly contemplated inert organic solvents include:

Liquid chlorinated hydrocarbons, liquid hydrocarbons and ethers, e.g. CCl₄, pentane, diethylthio.

The substituted carboxylic acid esters of formula (V) above can be prepared by contacting a compound of the formula

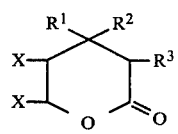 (IV)

wherein $R^1$, $R^2$, and $R^3$, are independently hydrogen or $C_1$ to $C_{10}$ alkyl and X is chlorine or bromine with a 0.8–1.5 fold stoichiometric amount of an alcoholate of formula (VII) in the presence of a superstoichiometric amount of an alkanol of formula (VIIa) below wherein R is an alkyl group of 1 to 4 carbon atoms and M is an alkali metal:

M—OR  (VII)

R—OH  (VIIa)

The reaction is preferably carried out at a temperature between −10° and +40° C.

There is further contemplated the preparation of an acetal of 2,2-dialkyl-3-formyl-cyclopropane carboxylic acid alkyl ester of the formula

from the substituted carboxylic acid ester of formula (V) above. In formula (VIII) above each R moiety is independently an alkyl group of 1 to 4 carbon atoms and each $R^1$, $R^2$, and $R^3$ group is independently hydrogen or an alkyl group of 1 to 10 carbon atoms. The same is prepared by contacting a lactone of formula (VI) supra with bromine or chlorine to obtain the corresponding dihalide of formula (IV). The dihalide is thereafter reacted with an alcoholate of formula (VII) in the presence of an alkanyl of formula (VIIa) supra whereby to form the corresponding acetal whose formula is

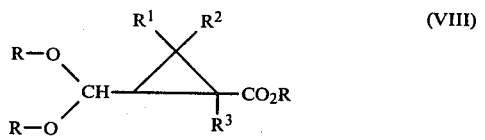

wherein each R group is independently an alkyl radical of 1 to 4 carbon atoms. The acetal of 2,2-dialkyl-3-formyl-cyclopropane carboxylic acid alkyl ester is in turn prepared by reacting the acetal prepared from the dihalo lactone with an alcoholate of the formula (VII) above whereby cyclization occurs and the cyclopropane carboxylic acid structure of formula (VIII) supra is formed. The cyclization reaction of the acetal of formula (V) is preferably effected at a temperature in the range of +30° to 150° C. It will be observed that in this series of reactions, it is not necessary that one of $R^1$, $R^2$ and $R^3$ be an alkyl group. In fact, all of the moieties $R^1$, $R^2$ and $R^3$ can be hydrogen, all of the moieties $R^1$, $R^2$ and $R^3$ can be alkyl or some of the moieties $R^1$, $R^2$ and $R^3$ can be alkyl while others are hydrogen.

Compounds of formula (IV) are prepared from the corresponding non-halogenated lactone whose formula is

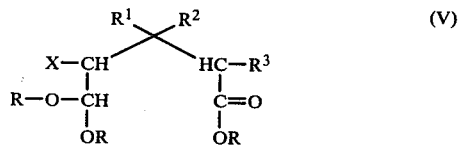

wherein $R^1$, $R^2$, and $R^3$ are hydrogen or the same or different alkyl group of 1 to 10 carbon atoms. These compounds can be prepared in the manner described above from a pentene carboxylic acid whose formula is

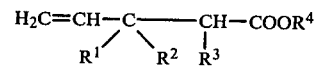

wherein each $R^1$, $R^2$ and $R^3$ is independently hydrogen or $C_1$ to $C_{10}$ alkyl group without the proviso that one of the groups $R^1$ to $R^3$ is an alkyl group. In such formula $R^4$ is a $C_1$ to $C_4$ alkyl group, hydrogen or an alkali metal or an alkaline earth metal. The compound in turn is reacted with chlorine or bromine under the conditions set forth above to saturate the ring and form the corresponding dihalo propane dicarboxylic acid (ester). The halogenation forms a compound of the formula

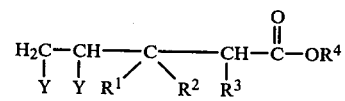

wherein each Y moiety is independently chlorine or bromine. The same when heated at 150° to 200° C. forms the corresponding lactone:

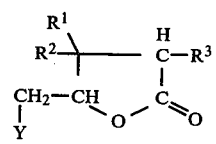

It will be observed that each moiety $R^1$, $R^2$ and $R^3$ is independently hydrogen or $C_1$–$C_{10}$ alkyl without the proviso that at least one of them is an alkyl group. When the lactone is reacted with the base it forms a corresponding epoxide also as set forth above with $R^1$, $R^2$, and $R^3$ being equal to hydrogen, preferably. The corresponding expoxide of the formula

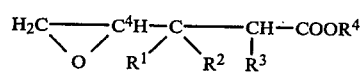

is in turn reacted with an acid to effect preparation of a compound of the formula

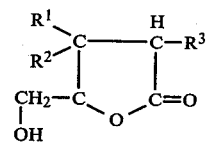

which in turn when heated at 200° to 500° C. forms an unsaturated cyclic structure of the formula

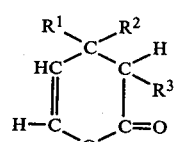

This compound in turn can react with a halogen to form the dihalo compound of formula (IV) supra.

The reaction to prepare a compound of formula (IV) and (V) as well as the use of the latter compound for the preparation of an acetal of 2,2-dialkyl-3-formyl-cyclopropane carboxylic acid ester of formula (VIII) above, follows the reaction scheme set forth below

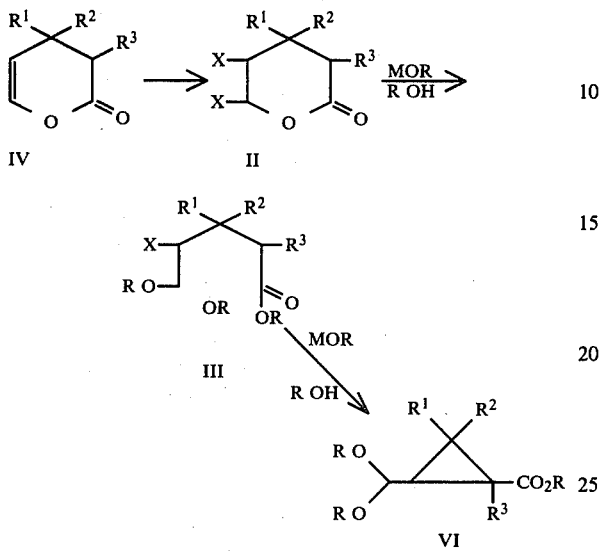

The halogen addition to the dihydro pyrone compound of formula (VI) is conducted in an inert organic reaction medium employing an inert organic solvent preferably a liquid chlorinated hydrocarbon such as carbon tetrachloride. The halogen, chlorine or bromine, is dosed into the reaction mixture at a temperture of between $-50°$ to $+40°$ C. Preferably, the temperature is between $-10°$ and $+40°$ C. At the end of the reaction the solvent is eliminated by distillation at reduced pressure such as vacuum induced by an aspirator using for example flowing water. In this manner the dihalo lactone of formula (IV) can be obtained and with or without further purification it can be employed to form the acetal by reaction of an alkali metal or alkaline earth metal alcoholate in the presence of an alkanol.

The dihalo lactone is thereafter reacted with 0.8 to 1.2 fold stoichiometric amount of an alcoholate of formula (VII) in the presence of a super stoichiometric amount of an alkanol of formula (VII) above, these being alcoholates and alcohols respectively whose alkyl group contains 1 to 4 carbon atoms. Preferably, the alcoholate is an alkali metal alcoholate especially sodium alcoholate e.g. sodium methylate. The reaction is conducted preferably at a temperature between $-10°$ and $+60°$ C. Preferably the temperature is between $-10°$ and $+40°$ C. The alcohol is employed in a stoichiometric excess preferably between 2 and 200 molar excess. The resultant acetal can be worked up by extraction with water and distillation of the raw material. If the reaction mixture contains no excess alcoholate, the same can be distilled directly after the reaction.

Cyclization to form the cyclopropane carboxylic acid ester of formula (VIII) above is effected with the help of the stoichiometric amount of a metal alcoholate of formula (IV). The reaction is performed in an reaction mixture preferably containing an organic solvent. For this purpose, an alcohol of the alcoholate can be employed, preferably. In addition, there can be employed as other inert solvents compositions such as diethyl ether. The cyclization is effected at a temperature between $+30°$ and $150°$ C. occasionally under pressure. Generally speaking, the pressure is between 1 and 10 atmospheres absolute. The cyclic compounds of formula (VIII) are obtained in a sis, transmixture.

The cyclic compounds of formula (VIII) can be prepared with or without isolation of the intermediate acetal. In this case 1.8 to 2.2 fold of stoichiometric amount of metal alcoholate of formula (V) is employed in the presence of a stoichiometric excess of alkanol of formula (VIIa), preferably employed in a 2 to 200 molar excess. The temperature will range from between $-10°$ to $+60°$ C. at the commencement of the reaction and temperatures of up to $+30°$ to $+150°$ C. will develop during the reaction. It is, however, also possible that the reaction is peformed without isolation of an intermediate product and the reaction is carried out at a temperature in the range of $+30°$ to $+60°$ C.

The compounds of the formula (VIII) can be used to prepare the free aldehyde. The free aldehyde is an important intermediate in preparation of insecticides of the Pyrethroid class. Such preparation is described e.g. in "Nature", London (1973), 144, 456.

EXAMPLE 1

12.7 g 3,3-dimethylpentene-4-carboxylic acid methylester is dissolved in 18.9 ml carbon tetrachloride, and 14.3 g bromine in 44.9 ml carbon tetrachloride is added dropwise to this mixture at from 10° to 20° C. After elimination of the solvent in vacuum, 3,3-dimethyl-4,5-dibromopentane carboxylic acid methyl ester is obtained in a nearly quantitative yield.

NMR spectrum (30 MHz, CCl$_4$): $\delta = 1.1$ (s, 3 H); 1.3 (s, 3 H); 2.4 (s, 2 H); 2.7 (s, 3 H); 3.3 to 4.7 (m, 3 H).

EXAMPLE 2

20.0 g 3,3-dimethyl-4,5-dibromopentane carboxylic acid methylester is refluxed in a fractional distillation apparatus for 30 minutes at a pressure of 0.8 mm and then fractionally distilled. At 95° to 96° C., 11.3 g dihydro-4,4-dimethyl-5-bromomethyl-(3 H)-furanone distills over.

NMR spectrum (100 MHz, CCl$_4$): $\delta = 1.10$ (s, 3 H); 1.26 (s, 3 H); 2.41 (m, 2 H); 3.55 (m, 2 H); 4.37 (m, 1 H).

EXAMPLE 3

43.7 g dihydro-4,4-dimethyl-5-bromoethyl-(3 H)-furanone is dissolved in 166 ml methanol, and after the addition of 11.4 g sodium methylate this mixture is refluxed for 5 hours. The methanol is eliminated in vacuum and the residue is dissolved in water. The aqueous solution is extracted with ether and the organic phase is dried through a molecular sieve and fractionally distilled. At a pressure of 13 mm and a temperature of 86° to 88° C., 29.5 g 4,5-epoxy-3,3-dimethylpentane carboxylic acid methyl ester distills over.

$^1$H-NMR spectrum (100 MHz, CCl$_4$): $\delta = 0.95$ (s, 3 H); 0.98 (s, 3 H); 2.22 (m, 2 H); 2.52 (m, 2 H); 2.77 (m, 1 H); 3.60 (m, 3 H).

EXAMPLE 4

21.1 g 4,5-epoxy-3,3-dimethylpentane carboxylic acid methyl ester is dissolved in 50 ml CCl$_4$ and the mixture is shaken for 5 hours with 12 ml 2 N H$_2$SO$_4$. The organic phase is then separated and the aqueous phase extracted with ether, and the combined organic phases are dried by the use of a molecular sieve. After elimination of the organic solvent, there remains a crystalline residue (17.6 g) which is identified as dihydro-4,4-dimethyl-5-hydroxymethyl-(3 H)-furanone. (Melting point, 40° to 42° C.)

$^1$H-NMR spectrum (100 MHz, CDCl$_3$): δ=1.08 (s, 3 H); 1.17 (s, 3 H); 2.37 (m, 2 H); 3.77 (m, 2 H); 4.15 (m, 1 H); 3.80 (bs, 1 H).

EXAMPLE 5

2 g dihydro-4,4-dimethyl-5-hydroxymethyl-(3 H)-furanone is dissolved in 20 ml toluene and this mixture is trickled under nitrogen, at a temperature of 300° C., over a period of 80 minutes through a heatable quartz tube 30 cm long and 2.2 cm in diameter which is filled with quartz spheres, and is collected in a cooled receiver. The toluene is eliminated at normal pressure by fractional distillation. The residue is distilled at 12 mm. 0.5 g 3,4-dihydro-4,4-dimethyl-α-pyrone (boiling point at 12 mm, 60° to 62° C.) is obtained. In addition, 1.3 g of starting product is recovered.

$^1$H-NMR spectrum (100 MHz, CCl$_4$): δppm=1.12 (s, 6 H); 2.40 (bs, 2 H); 5.11 (d, 1 H); 6.37 (d, 1 H).

EXAMPLE 6

10.0 g dihydro-4,4-5-bromomethyl-(3H)-furanone are refluxed with 3.0 g sodium methylate in 37 ml methanol for 5 hours. The solvent is eliminated in vacuum and the residue is dissolved in 20 ml H$_2$O and then extracted with ether. The ethereal phase is dried through a molecular sieve and the ether eliminated in vacuum. The residue is distilled at 20 mm. 6.4 g 4,5-epoxypentane carboxylic acid methyl ester (boiling point at 20 mm, 85° C.) is obtained.

EXAMPLE 7

6.0 g 4,5-epoxypentane carboxylic acid methyl ester is shaken in a mixture of 10 ml ether and 10 ml 2 n HCl for 1 hour. The ether is then separated and the aqueous phase perforated with ether. From the combined dried ethereal phases 3.7 g dihydro-5-hydroxymethyl-(3H)-furanone is obtained after removal of the ether in vacuum.

EXAMPLE 8

8.0 g dihydro-5-hydroxymethyl-(3H)-furanone are trickled at a temperature of 300° C. over a period of 80 minutes through a heatable quartz tube 30 cm long and 2.2 cm in diameter which is filled with montmorillonite-spheres, and are collected in a cooled receiver. 5.9 g 3,4-dihydropyrone are obtained.

$^1$H-NMR spectrum (30 MHz): ppm=2.0 3.0 (m, 4 H), 5.40 (m, 1 H), 6.65 (m, 1 H).

EXAMPLE 9

17.6 g 4,4-dimethyl-3,4-dihydro-α-pyrone are dissolved in 45.0 g CCl$_4$, and 22.3 g bromine in 59 g CCl$_4$, dissolved at 5° to 10° C., is added dropwise to this mixture under stirring. After the dropping in the solvent is removed in water-jet vacuum. 39.5 g crystalline 4,4-dimethyl-5,6-dibromo-δ-valerolactone are obtained. (Melting point 85°-87° C. from CCl$_4$).

$^1$H-NMR spectrum (100 MHZ, CCl$_4$): $_{ppm}$=1.16 (s, 3 H), 1.24 (s, 3 H), 2.70 (m, 2 H); centers at 4.32 and 4.41 (m, 1 H); centers at 6.46–6.61 (m, 1 H).

EXAMPLE 10

9.5 g 4,4-dimethyl-5,6-dibromo-δ-valerolactone are dissolved in 5.0 g methanol and 1.67 g Na-methylate, dissolved in 11.0 g methanol, are added dropwise for 2 hours under stirring at 20° to 30° C. Then the reaction mixture is poured into 50 ml H$_2$O and the water extracted with methylene chloride. After drying of the organic phase through a molecular sieve and removal of the solvent in water-jet vacuum 7.8 g 5,5-dimethoxy-4-bromo-3,3-dimethylpentanecarboxylic acid methyl ester are obtained.

$^1$H-NMR spectrum (30 MHZ, CCl$_4$): δ$_{ppm}$=1.20 (s, 6 H); 2.53 (s, 2 H); 3.45 (s, 6 H); 4.48 (s, 2 H).

EXAMPLE 11

6.2 g 5,5-dimethoxy-4-bromo-3,3-dimethylpentane carboxylic acid methyl ester are dissolved in 3.3 g methanol and a solution from 1.3 g Na-methylate and 8.2 g methanol is added dropwise to this mixture. Then the mixture is stirred for 15 hours at 50° C. Then the reaction mixture is dissolved in water, extracted with diethylether and the organic phase is dried. After removal of the ether in water-jet vacuum the residue is distilled. 3.55 g cis, trans-2,2-dimethyl-3-formyl-(dimethylacetale)-cyclopropane carboxylic acid methyl ester are obtained.

EXAMPLE 12

0.5 g 4,4-dimethyl-3,4-dihydro-α-pyrone are dissolved in 4.5 g tetrachloromethane and 0.3 g gaseous chlorine is intoduced into this mixture at 10° C. After removal of the solvent in water-jet vacuum 0.7 g cis, trans-4,4-dimethyl-5,6-dichloro-δ-valerolacetone is obtained.

$^1$H-NMR spectrum (30 MHZ, CCl$_4$): δ$_{ppm}$: 1.25 (bs, 6 H); 2.70 (bs, 2 H); 4.15; 4.20 (2 d, 1 H); 6.15–6.45 (2 d, 1 H).

EXAMPLE 13

166 g 4,4-dimethyl-5,6-dichlorovalerolacetone are dissolved in 124 g methanol at room temperature and a methanolic sodium-methylate solution (48 g NaOCH$_3$ in 247 g methanol) is added to this solution dropwise. The mixture is then stirred for 1 hour at room temperature. The methanol is removed in water-jet vacuum and the residue is distilled in high vacuum in small portions. 187.8 g 5,5-dimethoxy-4-chloro-3,3-dimethylpentane carboxylic acid methyl ester are obtained (boiling point 0.1 mm Hg 117°–119° C.).

$^1$H-NMR spectrum (80 MHZ, CDCl$_3$): δppm=1.19 (s, 6 H); 2.51 (m, 2 H); 3.43 (s, 3 H); 3.44 (s, 3 H); 3.66 (s, 3 H); 4,24 (d, 1 H); 4.50 (d, 1 H).

EXAMPLE 14

8.0 g 5,5-dimethoxy-4-chloro-3,3-dimethylpentane carboxylic acid methyl ester are stirred in 30 ml diethyleneglycol-dimethylether with 2.2 g NaOCH$_3$ for 5 hours at 110° C. The sodium chloride thus obtained is filtered off, washed with diethyl ether and the organic phases are combined. After removal of the diethyl ether in vacuum the diethylen glycol-ether is distilled off in water-jet vacuum and the residue is distilled in high vacuum. 5.2 g 2,2-dimethyl-3-formyl-(dimethylacetale)-cyclopropane carboxylic acid methyl ester are obtained.

EXAMPLE 15

17.6 g 4,4-dimethyl-3,4-dihydro-α-pyrone is dissolved in 45 g CCl$_4$, and to this mixture 22.3 g bromine in 59 g CCl$_4$, dissolved at 5° to 10° C., is added dropwise with stirring. Following this dropwise addition, the solvent is eliminated in a water-jet vacuum. 39.5 g of crystalline 4,4-dimethyl-5,6-dibromo-δ-valerolacetone is so obtained. (Melting point, 85° to 87° C. from CCl₄.)

¹NMR spectrum (100 MHz, CCl₄): $\delta_{ppm}$=1.16 (s, 3 H), 1.24 (s, 3 H), 2.70 (m, 2 H); centers at 4.32 and 4.41 (m, 1 H); centers at 6.46–6.61 (m, 1 H).

EXAMPLE 16

9.5 g 4,4-dimethyl-5,6-dibromo-δ-valerolactone is dissolved in 5 g methanol, and to this mixture 1.67 g sodium methylate, dissolved in 11 g methanol, is added drowpsie with stirring over a period of 2 hours at 20° to 30° C. The reaction mixture is then poured into 50 ml H₂O, which is then extracted with methylene chloride. After drying of the organic phase by the use of a molecular sieve and elimination of the solvent in a water-jet vacuum, 7.8 g 5,5-dimethoxy-4-bromo-3,3-dimethylpentane carboxylic acid methyl ester is obtained.

¹H-NMR spectrum (30 MHz, CCl₄): $\delta_{ppm}$=1.20 (s, 6 H); 2.53 (s, 2 H); 3.45 (s, 6 H), 4.48 (s, 2 H).

EXAMPLE 17

6.2 g 5,5-dimethoxy-4-bromo-3,3-dimethylpentane carboxylic acid methyl ester is dissolved in 3.3 g methanol and to this mixture a solution of 1.3 g sodium methylate and 8.2 g methanol is added dropwise. This mixture is stirred for 15 hours at 50° C. The reaction mixture is then dumped into water and extracted with diethyl ether, and the organic phase is dried. After elimination of the ether in a water-jet vacuum, the residue is distilled. 3.55 g cis,trans-2,2-dimethyl-3-formyl-(dimethylacetal)-cyclopropane carboxylic acid methyl ester is so obtained.

EXAMPLE 18

0.5 g 4,4-dimethyl-3,4-dihydro-α-pyrone is dissolved in 4.5 g tetrachloromethane, and into this mixture 0.3 g gaseous chlorine is introduced at 10° C. After elimination of the solvent in a water-jet vacuum, 0.7 g cis,trans-4,4-dimethyl-5,6-dichloro-δ-valerolactone is obtained.

¹H-NMR spectrum (30 MHz, CCl₄): $\delta_{ppm}$: 1.25 (bs, 6 H); 2.70 (bs, 2 H); 4.15; 4.20 (2 d, 1 H); 6.15–6.45 (2 d, 1 H).

EXAMPLE 19

166 g 4,4-dimethyl-5,6-dichlorovalerolactone is dissolved in 124 g methanol at room temperature, and to this solution a methanol solution of sodium methylate (48 g NaOCH₃ in 247 g methanol) is added dropwise. The mixture then is stirred for another hour at room temperature. The methanol is eliminated in a water-jet vacuum, and the residue is distilled in small portions in a high vacuum. 187.8 g 5,5-dimethoxy-4-chloro-3,3-dimethylpentane carboxylic acid methyl ester is so obtained. (Boiling point $_{0.1\ mm\ Hg}$: 117°–119° C.

¹H-NMR spectrum (80 MHz, CDCl₃): $\delta_{ppm}$=1.19 (s, 6 H); 2.51 (m, 2 H); 3.43 (s, 3 H); 3.44 (s, 3 H); 3.66 (s, 3 H); 4.24 (d, 1 H); 4.50 (d, 1 H).

EXAMPLE 20

8 g 5.5-dimethoxy-4-chloro-3,3-dimethylpentane carboxylic acid methyl ester is stirred in 30 ml diethylene glycol dimethyl ether with 2.2 g NaOCH₃ for 5 hours at 110° C. The sodium chloride formed is filtered off and washed with diethyl ether and the organic phases are combined. After elimination of the diethyl ether in a vacuum, the diethylene glycol ether is distilled off in a water-jet vacuum and the residue is distilled in a high vacuum. 5.2 g 2,2-dimethyl-3-formyl-(dimethylacetal)-cyclopropane carboxylic acid methyl ester is so obtained.

Lactones of the formula

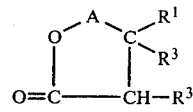

where at least one of R¹, R², and R³ is alkyl and A is

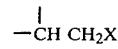

are useful for preparation of compounds of formula

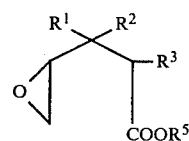

as indicated above when A is —CHYCHY— they are useful for preparation of compounds of the formula

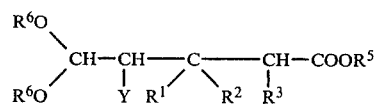

as indicated above when A is —HC=CH—, they are useful for the preparation of compounds of the formula

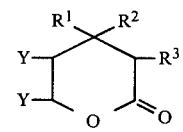

as indicated above.

A pentane carboxylic acid of the formula

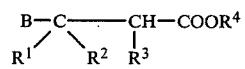

where R⁵ is C₁–C₄ alkyl, H or an alkali metal or alkaline earth metal and at least one of R¹, R² and R³ is alkyl, and B is

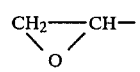

are useful as intermediates in the preparation compounds of the formula

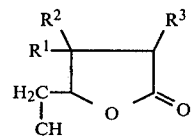

as indicated above, where B is $$\text{CH}_2\text{—CH—} \atop {\text{Y} \quad \text{Y}}$$

the compounds are useful as intermediates in the preparation of compounds of the formula

[structure: cyclopropane lactone with R¹, R², R³, H₂C, Y, O, =O, and —R³ where B is CH(OR⁶)—CH(OR⁶)Y]

the compounds are useful as: intermediates in the preparation of compounds of the formula

[structure: cyclopropane with R¹, R², R⁶O, R⁶O, HC—, COOR]

as indicated above.

When one of R¹, R² and R³ does not have to be alkyl and halosubstituted lactones of the formula

[structure: lactone with R¹, R², R³, X, X, O, =O]

i.e. where n=0 in formula IV are provided, they can be used as intermediates in the preparation of compounds of the formula

[structure: cyclopropane with R⁶—O, R⁶—O, CH—, COOR]

which are converted to insecticides in the analogue manner as described in "Nature", London (1973), 244, 456.

The acetal of 2,2-dialkyl-3-formyl-cyclopropanecarboxylic acid alkyl ester can be used as intermediate for the preparation of insecticides as mentioned below.

It can be converted to a pyrethroid insecticide by deacetelization in known manner to the corresponding aldehyde, which is converted by "Wittig-reaction" to the desired pyrethroid.

What is claimed is:

1. A substituted lactone of the formula

[structure: lactone ring with A, O, C, R¹, R², R³, H, O=C]

wherein A stands for —CHY—CHY—, Y being Cl or Br and R¹, R² and R³ are the same or different radicals from the group of hydrogen and $C_1$ to $C_{10}$ alkyl.

2. A substituted lactone according to claim 1, wherein only one of R¹, R² and R³ is alkyl.

3. A substituted lactone according to claim 1, wherein only two of R¹, R² and R³ are alkyl.

4. A substituted lactone according to claim 1, wherein each of R¹, R² and R³ are alkyl.

5. A substituted lactone according to claim 1, wherein R¹ and R² are different.

* * * * *

UNITED STATES PATENT AND TRADEMARK OFFICE
CERTIFICATE OF CORRECTION

PATENT NO. : 4,424,369           Page 1 of 2
DATED     : January 3, 1984
INVENTOR(S) : Hans-Georg Schmidt It is certified that error appears in the above-identified patent and that said Letters Patent is hereby corrected as shown below:

| | |
|---|---|
| Col. 1, line 32 | Before "=>CH" insert --A-- |
| Col. 1, line 32 | After "-CH$_2$" delete "A" and insert --X-- |
| Col. 3, line 26 | Delete "160" and insert --760-- |
| Col. 4, line 23 | Beginning of formula, delete "C" |
| Col. 5, line 18 | Add -- . -- after "lactone"; capitalize --With--; delete "." after "bond"; delete "This" and insert --this-- |
| Col. 5, line 30 | Delete "+" under "CH" and delete "2" after "CH$\mid$Y" |
| Col. 6, line 26 | Delete "acetats" and insert --acetals-- |
| Col. 6, line 30 | Delete "OR$^2$", two instances, and insert --OR$^6$--, two instances |
| Col. 6, line 53 | Delete "diethylthio" and insert --diethyl ether-- |
| Col. 8, line 45 | Middle of formula delete "C$^4$H" and insert --CH-- |

UNITED STATES PATENT AND TRADEMARK OFFICE
CERTIFICATE OF CORRECTION

PATENT NO. : 4,424,369

DATED : January 3, 1984

INVENTOR(S) : Hans-Georg Schmidt

It is certified that error appears in the above-identified patent and that said Letters Patent is hereby corrected as shown below:

| | |
|---|---|
| Col. 9, line 57 | Delete "material" and insert --product-- |
| Col. 10, line 23 | Delete "144" and insert --244-- |
| Col. 11, line 61 | Before "ppm" insert --δ-- |
| Col. 13, line 3 | Delete "¹NMR" and insert --¹H NMR-- |
| Col. 14, line 59 | After "preparation" insert --of-- |
| Col. 16, line 10 | Delete "the analogue" and insert --an analogous-- |

Signed and Sealed this

Eighth Day of May 1984

[SEAL]

Attest:

GERALD J. MOSSINGHOFF

Attesting Officer    Commissioner of Patents and Trademarks